United States Patent [19]

Anderson et al.

[11] 4,127,594

[45] Nov. 28, 1978

[54] SELECTIVE HYDROGENATION OF OLEFINIC IMPURITIES IN EPICHLOROHYDRIN

[75] Inventors: Elmer A. Anderson; Leo Kim; Sunny C. Tang, all of Houston, Tex.

[73] Assignee: Shell Oil Company, Houston, Tex.

[21] Appl. No.: 879,302

[22] Filed: Feb. 21, 1978

[51] Int. Cl.$^2$ ............................................. C07D 301/32
[52] U.S. Cl. ................................................. 260/348.37
[58] Field of Search ..................................... 260/348.37

[56] References Cited

U.S. PATENT DOCUMENTS 4,021,454    5/1977    Wulff et al. ..................... 260/348.29

*Primary Examiner*—Norma S. Milestone

[57] ABSTRACT

Beta-chloroacrolein and 5,6-epoxyhexene-1 impurities present in minor amounts in epichlorohydrin are selectively removed with minimal concomitant destruction of epichlorohydrin by hydrogenation in the presence of a catalyst comprising rhodium, platinum or palladium deposited on a non-acidic, refractory support.

7 Claims, No Drawings

SELECTIVE HYDROGENATION OF OLEFINIC IMPURITIES IN EPICHLOROHYDRIN

BACKGROUND OF THE INVENTION

This invention relates to a chemical method for removing certain difficult to remove olefinic impurities from epichlorohydrin. More particularly, this invention is directed to a catalytic hydrogenation process for selectively removing beta-chloroacroleins and 5,6-epoxyhexene-1 from a high purity epichlorohydrin stream e.g., greater than about 90% by weight epichlorohydrin, obtained by epoxidation of allyl chloride with an organic hydroperoxide in the presence of a catalyst of an inorganic oxygen compound of silicon in chemical combination with an oxide or hydroxide of titanium.

Epichlorohydrin is a material of commerce having particular utility as a starting material for the manufacture of epoxy resins. In the past, commercial routes to epichlorohydrin have been essentially based on the chlorohydrination of allyl chloride (addition of hypochlorous acid to allyl chloride to form a glycerol dichlorohydrin intermediate followed by alkali metal promoted dehydrohalogenation of the intermediate to epichlorohydrin). More recently, environmental constraints coupled with the energy situation have turned the industry's attention to alternative synthetic routes to epichlorohydrin which are more attractive from effluent handling and/or energy consumption standpoints. One alternate process having considerable appeal affords epichlorohydrin directly via the epoxidation of allyl chloride with an organic hydroperoxide in the presence of a heterogeneous, titanium based catalyst. In this process, which is broadly described in U.S. Pat. No. 4,021,454, a molar excess of allyl chloride is reacted with a hydrocarbon hydroperoxide such as ethylbenzene hydroperoxide or tertiary butyl hydroperoxide in the presence of a catalyst comprising an inorganic oxygen compound of silicon in chemical combination with an oxide or hydroxide of titanium to afford epichlorohydrin in high yield and selectivity with concomitant conversion of hydroperoxide to the corresponding alcohol. In a typical operation, the epichlorohydrin is recovered from the epoxidation reaction effluent by a series of distillations in which the excess allyl chloride and lighter impurities are initially removed as an overhead stream with the bottoms being passed to a second distillation where crude epichlorohydrin is separated from the alcohol product followed by one or more distillations to upgrade the crude epichlorohydrin e.g. by sequential removal of light and heavy end impurities, to give a purified material having a purity of greater than 95% by weight epichlorohydrin. After suitable upgrading, the excess allyl chloride recovered from the reaction effluent is recycled back to the epoxidation reaction zone and if desired, the alcohol can be recovered as a coproduct of the process or reconverted to hydroperoxide via procedures such as dehydration to olefin, hydrogenation of the olefin and oxidation to hydroperoxide.

While the aforementioned process employing a heterogeneous titanium containing epoxidation catalyst is quite attractive in terms of reduced energy consumption and the production of a smaller volume, more treatable aqueous effluent than the conventional chlorohydrination process, it is not devoid of problems. One problem area is the apparent unavoidable production of certain olefinic byproducts in the epoxidation and/or subsequent processing steps which closely resemble epichlorohydrin in physical properties and therefore are difficult, if not impossible, to remove by conventional physical separation techniques. These process byproducts, specifically cis- and trans-beta-chloroacroleins and 5,6-epoxyhexene-1, are present only in minor amounts in the recovered epichlorohydrin i.e., the combined impurity concentration typically being less than 2% by weight; however, stringent purity specifications for the finished epichlorohydrin coupled with certain undesirable traits of the impurities themselves, such as color and reactivity in end use applications of the finished epichlorohydrin, make efficient removal of these impurities almost essential.

From the foregoing, it is apparent that considerable advantage would be obtained if an economic and efficient technique could be developed for substantially complete removal of the beta-chloroacrolein and 5,6-epoxyhexene-1 impurities from the recovered epichlorohydrin. Further, it would be even more desirable if this removal of impurities could be effected with minimal destruction of the recovered epichlorohydrin.

SUMMARY OF THE INVENTION

An efficient and effective technique has now been found for removing beta-chloroacrolein and 5,6-epoxyhexene-1 impurities from epichlorohydrin produced by the aforementioned direct epoxidation process wherein allyl chloride is reacted with a hydrocarbon hydroperoxide in the presence of a heterogeneous catalyst comprising an inorganic oxygen compound of silicon in chemical combination with an oxide or hydroxide of titanium. In particular, it has been discovered that cis- and trans- beta-chloroacroleins and 5,6-epoxyhexene-1 which occur in minor amounts in recovered epichlorohydrin from the aforementioned process can be essentially completely removed by a hydrogenation process wherein the recovered epichlorohydrin, typically greater than 90% by weight epichlorohydrin, is treated with hydrogen under mild conditions in the presence of a catalyst comprising rhodium, platinum or palladium deposited on a non-acidic, refractory support. The process of the invention is particularly desirable in that the hydrogenation with the limited class of metal catalysts defined is sufficiently selective that the beta-chloroacrolein and 5,6-epoxyhexene-1 impurities can be essentially completely hydrogenated with little or no concomitant destruction of the epichlorohydrin present.

Accordingly, in its broadest aspects, the instant invention provides a process for selectively removing minor amounts of betachloroacroleins and 5,6-epoxyhexene-1 from a mixture made up predominatly of epichlorohydrin by treating said mixture with hydrogen at a temperature of between about 20° and about 150° C. in the presence of a supported catalyst comprising a metal selected from the class consisting of rhodium, platinum and palladium deposited on a non-acidic, refractory support, said metal being present at a concentration ranging from about 0.05 to about 10% by weight of the supported catalyst.

DESCRIPTION OF THE PREFERRED EMBODIMENTS

The process according to the invention is effective in selectively removing olefinic impurities such as beta-chloroacroleins and 5,6-epoxyhexene-1 from any process stream of mixture made up predominantly of epichlorohydrin with little or no concomitant loss of the epichlorohydrin. In particular, the process finds application in removing said olefinic impurities from epichlorohydrin which has been recovered using conventional separation techniques from an allyl chloride epoxidation carried out using a hydrocarbon hydroperoxide epoxidizing agent in the presence of a heterogeneous, titanium-containing catalyst, as described in U.S. Pat. No. 4,021,454. The reaction product of the process of this patent contains significant amounts of allyl chloride reactant and alcohol product from the hydroperoxide conversion in addition to the epichlorohydrin. In the typical processing scheme, the major components of the reaction product are separately recovered in crude form in a series of physical separation e.g., fractional distillation, steps. The crude epichlorohydrin recovered in this fashion may be treated directly using the process of the invention or further upgraded, as by sequential distillations to remove light and heavy end impurities, prior to selective hydrogenation in accordance with the invention. The epichlorohydrin stream treated with the process of the invention suitably contains at least 90% by weight epichlorohydrin and preferably from about 94% to about 99% by weight epichlorohydrin as is the case for the upgraded epichlorohydrin feedstock described above. The epichlorohydrin stream recovered from the epoxidation reaction in accordance with the aforementioned U.S. Pat. No. 4,021,454 may contain beta-chloroacrolein and 5,6-epoxyhexene-1 impurities at levels as high as about 2% by weight of the combined impurities based on the total weight of the recovered mixture. More typically, the level of beta-chloroacroleins (combined cis and trans) ranges between about 0.4% and about 0.9% by weight of the total mixture whereas the 5,6-epoxyhexene-1 falls between about 0.4% and 0.9% by weight of the total mixture.

The catalyst employed for the hydrogenation process of the invention is a supported particulate solid containing a metal selected from the class consisting of rhodium, platinum and palladium as the active catalytic agent deposited on a non-acidic, refractory support. The effectiveness of this limited class of metals in catalyzing the hydrogenation of the beta-chloroacrolein and 5,6-epoxyhexene-1 impurities is surprising in that a variety of other metals generally recognized as hydrogenation catalysts — e.g., Co, Ni, Cu, Ru and Re — were found to be ineffective in catalyzing the impurity hydrogenation (see Illustrative Embodiment I, below). Further, the selective nature of this catalytic hydrogenation deserves special recognition since the predominant component of the mixture treated i.e., epichlorohydrin, contains both a chlorine-carbon bond and an epoxide linkage which are known to be highly susceptible to hydrogenation. Of the three metals exhibiting hydrogenation activity, platinum and palladium are preferred from a standpoint of cost and availability with palladium being most preferred from a cost effectiveness standpoint. The three metals differ somewhat in inherent catalytic activity from the impurity hydrogenation, accordingly, the concentrations of metal employed on the support will depend on both the specific metal selected and the conditions for the hydrogenation. Generally, the metal loading on the support will range between about 0.05 and 10% by weight of the supported catalyst with metal concentrations in the range of about 0.3 to about 1.0% by weight of the supported catalyst being preferred. Typically, the concentration of platinum employed in the supported catalyst will be somewhat higher than that used for rhodium or palladium under equivalent reaction conditions since platinum appears to be somewhat less active than the other two metals in promoting the hydrogenation reaction.

The carrier material employed for the hydrogenation catalysts of the invention is a nonacidic, refractory material, suitably of particulate form, and may be of any desired shape such as spheres, flakes, tablets, extrusions, powders, granules, etc. To minimize decomposition of epichlorohydrin during the impurity hydrogenations it is important that the support employed be substantially non-acidic. In this regard, suitable carrier materials include aluminum oxides, carbon, charcoal, magnesia, silica, silicon carbide, fullers earth, selected clays, artificial and natural zeolites and synthetic polymeric materials such as polystyrene and polyacrylate adsorbent resins available commercially from Rohm and Haas Company under the trade designation "Amberlite XAD" polymeric resins. Although all forms of aluminum oxide conventionally employed as catalyst carriers appear to be acceptable supports for the catalysts of the invention, preference is given to alpha-alumina over higher surface area, more acidic aluminas such as gamma-alumina. Other preferred supports include carbon and Amberlite XAD-4, a polystyrene adsorbent resin available from Rohm and Haas. From a cost effectiveness standpoint, alpha-alumina is the most preferred carrier for the hydrogenation catalysts of the invention.

The hydrogenation catalysts employed in the process of the invention may be obtained for a variety of commercial sources or prepared using conventional techniques for preparation of supported metal catalysts. In this regard, a suitable catalyst preparation technique involves wet or dry impregnation of the carrier with an aqueous solution containing a reducible salt of one of the catalytic metals of the invention — e.g. rhodium, platinum or palladium nitrate — followed by drying, if required, and reduction under a hydrogen atmosphere. In the case of commercially obtained catalysts, pretreatment with hydrogen may also be desirable to insure that the metal is present in reduced or elemental form on the catalyst.

The hydrogenation of cis- and trans-beta-chloroacroleins and 5,6-epoxyhexene-1 in the presence of epichlorohydrin in accordance with the invention may be suitably carried out in batch or continuous fashion under conditions which are mild enough to avoid significant simultaneous hydrogenation of the epichlorohydrin present. In this regard, the hydrogenation is generally carried out by contacting the feed mixture containing epichlorohydrin and the beta-chloroacrolein and 5,6-epoxyhexene-1 impurities with the supported hydrogenation catalyst at a temperature of between about 20° and about 150° C. in the presence of sufficient hydrogen to chemically reduce the olefinic impurities. Essentially complete reduction of the olefinic impurities is typically obtained by maintaining the molecular hydrogen pressure at between about 10 and about 1000 psig on the reaction mixture during the period of reaction. Preferably, the reaction temperature is maintained at between about 60° and about 80° C. with corresponding hydrogen pressures being between about 200 and about 400 psig. The reaction time for batch hydrogenations according to the invention suitably range between 0.1 and 4 hours. In a preferred mode of operation, the hydrogenation according to the invention is carried out continuously by passing the feed mixture over a fixed bed of supported hydrogenation catalyst in the presence of hydrogen. In such a continuous reaction system, the feed mixture is suitably passed through the catalyst bed at a liquid hourly spaced velocity or LHSV (ml/ml/hr) of between about 0.1 and about 50 with a corresponding hydrogen flow rate of from about 0.01 to about 100 (mole $H_2$/hr). Most preferably, the hydrogenation reaction according to the invention as carried out continuously in a trickle phase operation where the reaction mixture is allowed to percolate at a relatively low flow rate through the catalyst bed in the presence of hydrogen. Suitable conditions for this most preferred mode of operation include feed mixture flow rates of about 2 to about 10 (LHSV) and hydrogen flow rates of about 0.1 to about 10 (mole $H_2$/hr).

The selective hydrogenation according to the invention converts substantially all of the 5,6-epoxyhexene-1 impurity present to the corresponding epoxyhexane whereas the cis and trans beta-chloroacroleins predominantly undergo dehydrohalogenation in preference to carbonyl hydrogenation. In a typical hydrogenation, up to 100% of the 5,6-epoxyhexene-1 and 100% of the beta-chloroacroleins can be eliminated with less than 0.5% concomitant destruction of epichlorohydrin. The hydrogenated chloroacrolein products (predominantly propionaldehyde), can be readily removed from the product epichlorohydrin by conventional techniques such as distillation. The 1,2-epoxyhexane more closely resembles epichlorohydrin in physical properties and thus is more difficult to remove by physical separation techniques. However, with elimination of the olefinic bond, this impurity has less potential to react and interfer with downstream processing of the product epichlorohydrin.

The hydrogenation catalysts according to the invention and their use in selectively hydrogenating beta-chloroacrolein and 5,6-epoxyhexene-1 impurities in epichlorohydrin will be further described in the following illustrative embodiments.

ILLUSTRATIVE EMBODIMENT I

A series of batch reactions were carried out in Fisher Porter vessels using 0.1 g each of various commercially obtained metal catalysts known to have hydrogenation activity in various applications and 30 ml of an epichlorohydrin feed containing 97.5% by weight epichlorohydrin, 0.89% by weight 5,6-epoxyhexene-1, 0.55% by weight cis-beta-chloroacrolein and 0.34% by weight trans-beta-chloroacrolein as determined by gas chromatography. The hydrogen pressure employed in all cases was 100 psig $H_2$ and in most cases except as noted, the hydrogenations were conducted initially at 50° C. for 2 hours, a 10 ml sample removed, and the remaining 20 ml sample hydrogenated at a higher temperature (70° or 80° C. for 1 additional hour). The qualitative results from the hydrogenations are given in Table I, including the chemical identities of the catalysts tested with more detailed and quantitative results being given for some of the better catalysts in Table II. In this table product analysis reported was also determined by gas chromatography.

TABLE I

Summary of Catalyst Activity for the Hydrogenation of Epichlorohydrin Containing 5,6-Epoxyhexene-1 and Beta-chloroacrolein Impurities

| Metal Type | Catalyst Employed | Level of Catalyst Activity Observed[a] |
|---|---|---|
| Cobalt | Raney Co | N.R. |
|  | Co/kieselguhr | N.R. |
|  | CoO/MoO/$Al_2O_3$ | N.R. |
| Copper | $CuCr_2O_3$ | N.R. |
| Nickel | Ni/C | N.R. |
|  | Raney Ni | N.R. |
| Palladium | 5% Pd/$Al_2O_3$ | Good |
|  | 1% Pd/$SiO_2$ | Fair |
|  | 5% pd/C | Good |
| Platinum | 5% Pt/$Al_2O_3$ | Good |
|  | 5% Pt/C | Poor |
|  | 5% PtS/C | Poor |
|  | 0.5% Pt/$SiO_2$ | Poor |
|  | 1% Pt/MgO | Some |
| Rhenium | 5% Re/$Al_2O_3$ | N.R. |
| Rhodium | 5% Rh/$Al_2O_3$ | Good |
|  | 5% Rh/C | Good |
|  | 1% Rh/$SiO_2$ | N.R. |
| Ruthenium | 5% Ru/C | N.R. |
|  | 5% Ru/$Al_2O_3$ | N.R. |

[a]Abbreviation N.R. is this column stands for no reaction.

TABLE II

| Catalyst Employed | Reaction Conditions Temp. °C | Time hr | Hydrogenation Product Analysis % Weight |  |  |  |
|---|---|---|---|---|---|---|
|  |  |  | 5,6-EP[a] | cis-CLAN[b] | tr-CLAN[c] | Epoxide[d] |
| 5% Rh/$Al_2O_3$ | 50 | 2 | 0.06 | 0.12 | 0.12 | 98.3 |
|  | 70 | 1 | 0.02 | 0.06 | 0.09 | 98.5 |
| 5% Rh/C | 50 | 2 | 0.04 | 0.07 | 0.16 | 97.8 |
|  | 70 | 1 | 0.05 | 0.06 | 0.02 | 97.5 |
| 5% Pt/$Al_2O_3$ | 50 | 2 | 0.04 | 0.09 | 0.17 | 98.0 |
|  | 70 | 1 | 0.03 | 0.06 | 0.06 | 97.2 |
| 5% Pd/C | 50 | 2 | 0.17 | 0.02 | 0.04 | 97.5 |
|  | 80 | 1 | 0.04 | 0.00 | 0.00 | 97.7 |
| 5% Pd/$Al_2O_3$[e] | 22 | 2 | 0.02 | 0.00 | 0.00 | 95.4 |

[a]5,6-epoxyhexene-1
[b]cis-beta-chloroacrolein
[c]trans-beta-chloroacrolein
[d]epichlorohydrin
[e]analysis of epichlorohydrin feedstock used for this catalyst test: epichlorohydrin - 96.1% by weight, cis-beta-chloroacrolein - 0.41% by weight, trans-beta-chloroacrolein - 0.21% by weight, 5,6-epoxyhexene-1- 0.43% by weight.

ILLUSTRATIVE EMBODIMENT II

A 5% rhodium catalyst supported on a commercially available macroreticular polystyrene adsorbent resin (Amberlite XAD-4 from Rohm and Haas Company) was prepared for testing in the process of the invention using the following technique. An aqueous solution of Rh($NO_3$)$_3$.2$H_2O$ (2.0 g) in 3 ml of deionized water was stirred with 11.0 g of Amberlite XAD-4 for 10 minutes. The resultant particulate solid was then reduced in a 100 ml stainless steel autoclave under 1750 psi $H_2$ at 170° C. for 2 hours to yield about 13 g of Rh/XAD-4 with an approximate 5% by weight metal loading.

Using the same preparation technique a Palladium on Amberlite XAD-4 polystyrene absorbent resin catalyst was also prepared. In this case an aqueous solution of Pd($NO_3$)$_2$ was used to give, on hydrogenation, a Pd/XAD-4 catalyst having an approximate 5% by weight metal loading.

The two catalysts prepared as above were then tested as hydrogenation catalysts in the process of the invention using the batch reaction technique described in Illustrative Embodiment I. On a qualitative basis, the 5% Pd/XAD-4 catalyst showed good activity in catalyzing the selective hydrogenation of 5,6-epoxyhexene-1 and beta-chloroacrolein impurities while no reaction was observed with the 5% Rh/XAD-4 catalyst.

ILLUSTRATIVE EMBODIMENT III

To demonstrate the utility of the selective hydrogenation process of the invention on a continuous reactant flow basis, a series of experiments were carried out with commerically available, supported rhodium, palladium and platinum catalysts using various epichlorohydrin feed mixtures contaminated with 5,6-epoxyhexene-1 and beta-chloroacrolein impurities. The tests were conducted under trickle-phase flow conditions in glass lined reactor tubes containing supported catalysts which were pretreated under hydrogen flow at 500° C. for 1 hour. The conditions for the hydrogenation were varied over a range of conditions with each catalyst. The reaction conditions employed with each catalyst together with the feed mixture composition treated and the results obtained are given in Table III below. The feed mixture and product analysis reported were determined by Gas Chromatography.

What is claimed is:

1. A process for selectively removing minor amounts of beta-chloroacroleins and 5,6-epoxyhexene-1 from a mixture made up predominantly of epichlorohydrin which comprises treating said mixture with hydrogen at a temperature of between about 20° C. and about 150° C. in the presence of a supported catalyst comprising a metal selected from the class consisting of rhodium, platinum and palladium deposited on a non-acidic, refractory support, said metal being present at a concentration ranging from about 0.05 to about 10% by weight of the supported catalyst.

2. The process according to claim 1, wherein the mixture subject to treatment with hydrogen contains at least 90% by weight epichlorohydrin and no more than 2% by weight of beta-chloroacroleins and 5,6-epoxyhexene-1 based on the combined weight of beta-chloroacroleins and 5,6-epoxyhexene-1 in the mixture.

3. The process according to claim 2, wherein the mixture treated contains from about 90% to about 100% by weight epichlorohydrin and between about 0.1% and about 1% by weight beta-chloroacroleins and from about 0.1% to about 1% by weight 5,6-epoxyhexene-1.

4. The process according to claim 2 wherein the non-acidic, refractory support is selected from the class consisting of alpha-alumina, carbon and a macroreticular polystyrene adsorbent resin.

5. The process according to claim 4 wherein the support is alpha-alumina.

TABLE III

| Catalyst Tested | Reaction Conditions | | | Product Analysis % by Weight | | | |
|---|---|---|---|---|---|---|---|
| | LHSV | Temp. °C | Pressure Psi $H_2$ | 5/6EP[a] | cis-CLAN[b] | tr-CLAN[c] | Epoxide[d] |
| 0.5% Pd/C[e] | 1 | 22 | 100 | 0.05 | 0.00 | 0.00 | 96.9 |
| | 2 | 22 | 100 | 0.07 | 0.04 | 0.04 | 97.9 |
| | 2 | 22 | 400 | 0.05 | 0.02 | 0.015 | 97.6 |
| | 5 | 50 | 100 | 0.08 | 0.015 | 0.015 | 99.2 |
| | 10 | 50 | 100 | 0.08 | 0.10 | 0.08 | 100.0 |
| | 10 | 60 | 100 | 0.07 | 0.07 | 0.06 | 96.0 |
| | 10 | 80 | 200 | 0.06 | 0.00 | 0.00 | 96.4 |
| 0.5% Pd/$\gamma$-$Al_2O_3$[f] | 1 | 22 | 100 | 0.02 | 0.00 | 0.00 | 84.3 |
| | 2 | 22 | 100 | 0.05 | 0.03 | 0.015 | 93.0 |
| | 2 | 50 | 100 | 0.00 | 0.02 | 0.00 | 90.1 |
| | 5 | 22 | 100 | 0.13 | 0.02 | 0.006 | 95.7 |
| | 10 | 22 | 200 | 0.13 | 0.02 | 0.015 | 96.0 |
| 0.3% Pd/$\gamma$-$Al_2O_3$[g] | 2 | 60 | 200 | 0.04 | 0.03 | 0.02 | 92.2 |
| | 5 | 60 | 200 | 0.04 | 0.03 | 0.02 | 94.8 |
| | 10 | 60 | 200 | 0.04 | 0.04 | 0.04 | 93.6 |
| 1.0% Pd/$\gamma$-$Al_2O_3$[g] | 5 | 60 | 200 | 0.03 | 0.02 | 0.00 | 91.5 |
| | 10 | 60 | 200 | 0.05 | 0.03 | 0.03 | 92.9 |
| | 15 | 60 | 200 | 0.05 | 0.04 | 0.04 | 94.7 |
| 0.5% Pd/$\alpha$-$Al_2O_3$[g] | 2 | 60 | 200 | 0.02 | 0.03 | 0.02 | 95.2 |
| | 5 | 60 | 200 | 0.04 | 0.04 | 0.02 | 95.0 |
| | 10 | 60 | 200 | 0.05 | 0.07 | 0.06 | 94.0 |
| 1.0% Pd/$\alpha$-$Al_2O_3$[g] | 5 | 60 | 200 | 0.05 | 0.04 | 0.04 | 94.2 |
| | 10 | 60 | 200 | 0.06 | 0.04 | 0.03 | 93.7 |
| | 15 | 60 | 200 | 0.10 | 0.07 | 0.07 | 94.1 |
| 0.25 Rh/$Al_2O_3$[h] | 1 | 50 | 100 | 0.19 | 0.07 | 0.06 | 93.8 |
| | 1 | 50 | 500 | 0.12 | 0.05 | 0.03 | 96.7 |
| | 1 | 70 | 500 | 0.04 | 0.09 | 0.04 | 97.7 |
| | 1 | 90 | 500 | 0.42 | 0.08 | 0.03 | 97.3 |
| | 2 | 50 | 100 | 0.14 | 0.07 | 0.05 | 97.1 |
| | 2 | 50 | 200 | 0.14 | 0.10 | 0.07 | 97.6 |
| | 2 | 70 | 100 | 0.08 | 0.02 | 0.02 | 96.8 |
| 0.5% Pt/$Al_2O_3$[f] | 2 | 50 | 100 | 0.00 | 0.02 | 0.00 | 90.1 |
| | 2 | 50 | 100 | 0.01 | 0.03 | 0.01 | 88.4 |

[a] 5,6-Epoxyhexene-1.
[b] Cis-beta-chloroacrolein.
[c] Trans-beta-chloroacrolein.
[d] Epichlorohydrin.
[e] Feed mixture composition used for tests with this catalyst: 5,6-epoxy-hexene-1 - 0.43% by weight, cis-beta-chloroacrolein - 0.41% by weight and trans-beta-chloroacrolein - 0.21% by weight, epichlorohydrin - 96.1% by weight.
[f] Feed mixture composition used for tests with this catalyst: 5,6-epoxy-hexene-1 - 0.43% by weight, cis-beta-chloroacrolein - 0.13% by weight and trans-beta-chloroacrollein - 0.10% by weight, epichlorohydrin - 94.5% by weight.
[g] Feed mixture composition used for tests with this catalyst: 5,6-epoxy-hexene-1 - 0.36% by weight, cis-beta-chloroacrolein - 0.20% by weight and trans-beta-chloroacrolein - 0.16% by weight, epichlorohydrin - 94.7% by weight.
[h] Feed mixture composition used for tests with this catalyst: 5,6-epoxy-hexene-1 - 0.89% by weight, cis-beta-chloroacrolein - 0.55% by weight and trans-beta-chloroacrolein - 0.34% by weight, epichlorohydrin - 97.5% by weight.

6. The process according to claim 5 wherein the catalyst is palladium on alpha-alumina.

7. The process according to claim 2 wherein the treatment with hydrogen is carried out continuously by passing the feed mixture through a fixed bed of supported catalyst in the presence of hydrogen at a liquid hourly space velocity of between about 0.1 and about 50 (ml/ml/hr) and a corresponding hydrogen flow rate of from about 0.01 to about 100 mole $H_2$/hour.

* * * * *